US010525278B2

(12) United States Patent
Wasserbauer et al.

(10) Patent No.: US 10,525,278 B2
(45) Date of Patent: Jan. 7, 2020

(54) LIGHT BASED THERAPY DEVICES AND METHODS

(71) Applicant: Hair Group, LLC, Walnut Creek, CA (US)

(72) Inventors: John Wasserbauer, Castro Valley, CA (US); Sara Wasserbauer, Alamo, CA (US); Erik Carlson, Alamo, CA (US)

(73) Assignee: Hair Group, LLC, Walnut Creek, CA (US)

( * ) Notice: Subject to any disclaimer, the term of this patent is extended or adjusted under 35 U.S.C. 154(b) by 0 days.

(21) Appl. No.: 15/677,840

(22) Filed: Aug. 15, 2017

(65) Prior Publication Data
US 2019/0054311 A1    Feb. 21, 2019

(51) Int. Cl.
*A61N 5/06*    (2006.01)
*A61B 18/20*    (2006.01)

(52) U.S. Cl.
CPC .......... *A61N 5/0617* (2013.01); *A61B 18/203* (2013.01); *A61B 2018/2065* (2013.01); *A61N 5/062* (2013.01); *A61N 2005/0652* (2013.01); *A61N 2005/0662* (2013.01)

(58) Field of Classification Search
CPC ................. A61N 5/0617; A61N 5/062; A61N 2005/0652; A61B 18/203; A61B 2018/2065
See application file for complete search history.

(56) References Cited

U.S. PATENT DOCUMENTS

| 281,340 A | 7/1883 | Campbell |
| 326,363 A | 9/1885 | Weston |
| 520,148 A | 5/1894 | William |
| 6,162,211 A | 12/2000 | Tankovich et al. |
| 6,176,854 B1 | 1/2001 | Cone |

(Continued)

FOREIGN PATENT DOCUMENTS

| AU | 2013201772 | 10/2014 |
| CA | 2400395 | 8/2001 |

(Continued)

*Primary Examiner* — Lynsey C Eiseman
*Assistant Examiner* — Jessandra F Hough
(74) *Attorney, Agent, or Firm* — Levine Bagade Han LLP (57) ABSTRACT

The present invention relates to a light therapy device article of manufacture, system and method for providing light is delivered to the skin by means of one or more optical fibers in therapeutic dosages from light source in wavelengths of 614-624 nm, 668-684 nm, 751-772 nm, and 813-846 nm. The light source may be comprised from one or more light emitting diodes LED disposed on a flexible printed circuit board (PCB) and ferrule adapter assembly configured to deliver light to the skin directly of the patient from the light source disposed on the PCB adjacent a scalp surface. A control circuit operably connected to the PCB is adapted to provide energy to one or more zones of LEDs to address hair loss treatment regimen including splotchy balding, receding hairline balding, crown balding and total scalp surface therapy. Accordingly, a portable, cordless, hands-free light therapy device may configured as a headdress to be worn by the patient to minimize the negative psychological association of hair loss, while still providing effective hair growth treatment at an affordable price.

21 Claims, 8 Drawing Sheets

(56) References Cited

U.S. PATENT DOCUMENTS

| | | |
|---|---|---|
| 6,283,956 B1 | 9/2001 | McDaniel |
| 6,497,719 B2 | 12/2002 | Pearl et al. |
| D472,969 S | 4/2003 | Wilden |
| 6,629,971 B2 | 10/2003 | McDaniel |
| 6,853,656 B1 | 2/2005 | Rnvig et al. |
| 6,916,316 B2 | 7/2005 | Jay |
| 7,201,764 B2 | 4/2007 | Pearl et al. |
| 7,214,222 B2 | 5/2007 | Yamazaki et al. |
| 7,331,964 B2 | 2/2008 | Maricle et al. |
| 7,722,655 B2 | 5/2010 | Lee |
| 8,048,135 B2 | 11/2011 | Cerullo, Jr. et al. |
| 8,702,771 B1 | 4/2014 | Frost |
| 8,771,327 B2 | 7/2014 | Pearl et al. |
| 9,132,279 B2 | 9/2015 | Roersma et al. |
| 2002/0123746 A1 | 9/2002 | McDaniel |
| 2002/0128696 A1 | 12/2002 | Pearl et al. |
| 2003/0093915 A1 | 5/2003 | Pearl et al. |
| 2004/0092918 A1* | 5/2004 | Jay .................. A61B 18/203 606/9 |
| 2004/0138727 A1* | 7/2004 | Taboada ............ A61N 5/0613 607/88 |
| 2004/0153131 A1 | 8/2004 | Yorke |
| 2004/0186536 A1 | 9/2004 | Osendowski |
| 2007/0179573 A1 | 8/2007 | Laurent |
| 2008/0004565 A1 | 1/2008 | Streeter et al. |
| 2008/0021528 A1 | 1/2008 | Carullo, Jr. et al. |
| 2008/0269732 A1 | 10/2008 | Pyun |
| 2009/0210037 A1 | 8/2009 | Roersma et al. |
| 2009/0274488 A1* | 11/2009 | Sugiyama ............ B41J 2/447 399/217 |
| 2010/0106077 A1* | 4/2010 | Rabin ................. A61N 5/0616 604/20 |
| 2011/0022132 A1 | 1/2011 | Kim |
| 2011/0087310 A1 | 4/2011 | Chen et al. |
| 2011/0092863 A1 | 4/2011 | Kim et al. |
| 2014/0236269 A1 | 8/2014 | Chen et al. |
| 2014/0296946 A1* | 10/2014 | Malek ................ A61N 5/0617 607/89 |
| 2014/0330196 A1 | 11/2014 | Ingman et al. |
| 2015/0112411 A1* | 4/2015 | Beckman .......... A61N 5/0616 607/90 |
| 2015/0224339 A1 | 8/2015 | Unger |
| 2016/0301190 A1 | 10/2016 | Lee et al. |

FOREIGN PATENT DOCUMENTS

| | | |
|---|---|---|
| CN | 2768826 | 4/2006 |
| CN | 1953717 | 4/2007 |
| CN | 200945318 | 9/2007 |
| CN | 200976922 | 11/2007 |
| CN | 200998533 | 1/2008 |
| CN | 101125233 | 2/2008 |
| CN | 101856543 | 10/2010 |
| CN | 201676413 | 12/2010 |
| CN | 201783099 | 4/2011 |
| CN | 201791270 | 4/2011 |
| CN | 203609762 | 5/2014 |
| CN | 203609768 | 5/2014 |
| CN | 203694428 | 7/2014 |
| CN | 204147241 | 2/2015 |
| CN | 204743002 | 11/2015 |
| DE | 102005034971 | 2/2006 |
| EP | 159446 | 10/1985 |
| EP | 1453431 | 9/2015 |
| JP | 2003116905 | 4/2003 |
| JP | 2003144561 | 5/2003 |
| JP | 3939953 | 7/2007 |
| KR | 20050110573 | 11/2005 |
| KR | 100761092 | 9/2007 |
| KR | 100818123 | 3/2008 |
| KR | 100818124 | 3/2008 |
| KR | 100851621 | 8/2008 |
| KR | 101045214 | 6/2011 |
| KR | 20110104616 | 9/2011 |
| KR | 20110113970 | 10/2011 |
| KR | 101126556 | 3/2012 |
| KR | 20120022151 | 3/2012 |
| WO | WO 2001/060457 | 8/2001 |
| WO | WO 2005/086846 | 9/2005 |
| WO | WO 2005/115263 | 12/2005 |
| WO | WO 2009/008967 | 1/2009 |
| WO | WO 2009/075410 | 6/2009 |
| WO | WO 2009/131420 | 10/2009 |
| WO | WO 2010/110861 | 9/2010 |
| WO | WO 2011/107628 | 9/2011 |
| WO | WO 2012/158762 | 11/2012 |
| WO | WO 2014/193029 | 12/2014 |

* cited by examiner

LIGHT BASED THERAPY DEVICES AND METHODS

BACKGROUND OF THE INVENTION

The present invention relates to designs, systems and methods of a light therapy device.

The concept of using light energy to treat human tissues has emerged in the last few decades. Radiation, UV, and broad spectrum light have all been employed therapeutically and efficaciously, enjoying wide acceptance in the medical community. One version of this, called Low Level Light Therapy (LLLT), uses a wide variety of wavelengths in the visible and near-infrared spectrum to generate a tissue response in a process that has become known as photobiomodulation. The potential list of applications for LLLT is enormous; everything from dental treatments to pain control and accelerated wound healing has been studied with promising results. Given the low incidence of side effects, ability to target specific tissues, and the relative ease of treatment, patient and physician acceptance and adoption of these technologies is justifiably growing.

The method of delivery has been problematic, however. Due to its coherent, single wavelength output and directionality, the laser diode is a commonly used light source, allowing practitioners to easily direct the beam to the target. Another potential source, the light emitting diode (LED), can also be used to generate light in a specific band of wavelengths, but with a much broader emission pattern. For completeness, we note that it is possible to generate either narrow or broad spectral ranges with a white light source and a filter. It has yet to be established whether narrow or broader emission spectra or coherent or incoherent light is more effective to induce photobiomodulation. The issue with all of the light sources is that human tissue, such as skin, can be highly reflecting. Furthermore, the presence of hair on the skin can cause significant absorption of the light intended for the skin. These two effects make it difficult to precisely control dosing during therapeutic applications. Since light can be scattered, absorbed, transmitted, or reflected, the light applied during certain LLLT applications should either be on the surface of the target, or be very close to be absorbed.

One major application of LLLT is to treat hair loss. Also known as alopecia, hair loss can be found in every country and has unfavorable social connotations in all cultures worldwide. Male pattern hair loss, or androgenetic alopecia, accounts for 95% of alopecia in males, with 70% of American men experiencing some form of hair loss by age 35. Female hair loss, while it is often more complex in etiology, affects a similarly large portion of women worldwide, with some estimates ranging from 1:4 in the United States (25%), to over 80% of women past the age of 60 (when hormones like estrogen drop). There is no cure for male or female pattern hair loss.

Unfortunately, the list of proven medical therapies that will help even the most common causes of hair loss is a short one. In the United States, men and women can use minoxidil (2% and 5%) in both liquid and foam forms, but this medication requires twice daily application and is considered distasteful and inconvenient by many. Men have the additional benefit of being able to use the daily oral medication finasteride, which can be extremely effective. There is a widespread misunderstanding regarding its side effect profile, however, since it can transiently affect libido (2.1-3.8% incidence), which hinders its adoption. Surgical hair restoration is effective, but it is expensive, and, as a result, unavailable to many patients.

Photobiomodulation is a recent addition to the existing FDA-approved hair loss armamentarium. LLLT in the wavelengths of 614-624 nm, 668-684 nm, 751-772 nm, and 813-846 nm, has been proven to reduce inflammation in the scalp, stimulate the release of growth factors in the hair follicle, up-regulate the production of ATP (the energy source for the cell), and increase oxygen levels and blood flow via a vasodilatory effect. Devices of all sorts including combs, helmets, handheld "massager-type" units, and hoods all have gained 510K clearance to be sold with the claim that they grow hair.

Currently, none of the published studies of these devices conforms to the wavelengths of light known to produce increased cellular activity in the hair follicle, and few of them even produce light within these known wavelength ranges. Furthermore, many light therapy devices deliver light to the skin from a distance or from above the hair. Such light may be absorbed by the presence of hair follicles, thereby limiting the available dose. Even if hair is not initially present, if hair growth occurs during the use of such LLLT devices, the light therapy process will be self-limiting. For these reasons, many existing LLLT device solutions for hair growth are sub-optimal at best, and ineffective at worst. Also, dosing time and frequency recommendations vary among devices, leading to sub-optimal treatments. Another concern with conventional devices arises when the device causes heating of the targeted region of the scalp, excessive heating can decrease the results of the therapy, leading to the potential for sub-optimal dosing. Based on the above, there is room for improved systems, devices, and methods for application of LLLT therapy.

BRIEF SUMMARY OF THE INVENTION

A variation of the improved systems, methods, and devices for providing LLLT devices. In one aspect, such devices are suited for hair growth by applying light delivery to the skin using one or more illumination sources. For example, the illumination source can comprise coherent light (e.g., laser), incoherent (e.g. LED, white light plus filter), filtered light, or a combination thereof. The illumination provided by the illumination source can be of a wavelength or wavelength range that is of beneficial and therapeutic value. The illumination source can comprise a source that transmits light from another location (e.g., an optical fiber) that generates the illumination, or the illumination source can also directly generate the illumination (such as an LED component). In some variations, the illumination source delivers the light to the treatment area via direct contact with the skin. In other variations, the illumination source delivers light to the treatment area just above the skin. In certain applications, positioning of the illumination source close to the tissue being treated such that the light delivery bypasses the interference that even short hair shafts above the skin create. Such close delivery allows for predicable and known dosing intensity and distribution, which enables standardized dosing. In certain variations of the devices and methods, it is desirable to prevent heat from increasing at the treated region. Therefore, the heat generated by the light sources can be kept away from the skin and to avoid a significant increase the temperature of the skin. A cooling scheme can also be used to either preserve the output power and efficiency of the light source itself or to cool the treated tissue.

Variations of the device and system include illumination sources that are shaped for patient comfort and/or to distribute the light around the delivery or contact point. In additional variations, a projecting element that includes or carries the illumination source is actuated so as to allow conformal contact with the skin. In an exemplary embodiment, an array of such projection elements having illumination sources are used to illuminate a substantial area of skin, such as the scalp. An advanced passive cooling scheme is used to preserve the output power and efficiency of the light sources. Advantageously, the present invention delivers light directly to the skin bypassing interference from hair follicles, thereby allowing for a known dosing intensity and distribution. The configurations described herein can provide an improvement in light delivery to the targeted region—one that reduces loss of energy to undesired absorption and reflection and that ensures maximum absorption by the target tissue, thereby enabling standardized dosing. Variations of the devices described herein can also allow delivery of light at or very close to the skin/scalp, which allows bypassing the interference that even short hair shafts above the skin create, and minimizing the effect of reflection. Second, it would deliver light in one of the four optimum wavelength ranges.

Variations of the device also allow for a hands-free, cordless, and portable, with an interactive feedback component that allows a patient to monitor their progress, further improving adherence with the treatment regimen. Such variations also time the treatments and help patients manage dosing frequency with a minimal amount of external visibility. Cell proliferation (i.e. growth of hair) is optimized with low doses over longer periods of time. So, the present LLLT device allows for convenient and frequent dosing (at least 2-3 times per week, if not daily).

BRIEF DESCRIPTION OF THE SEVERAL VIEWS OF THE DRAWINGS

Non-limiting and non-exhaustive embodiments of the present invention are described with reference to the following drawings. In the drawings, like reference numerals refer to like parts throughout the various figures unless otherwise specified.

DETAILED DESCRIPTION OF THE INVENTION

For a better understanding of the present invention, reference will be made to the following Description of the Embodiments, which is to be read in association with the accompanying drawings, which are incorporated in and constitute a part of this specification, show certain aspects of the subject matter disclosed herein and, together with the description, help explain some of the principles associated with the disclosed implementations.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising. (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

Figure 1:
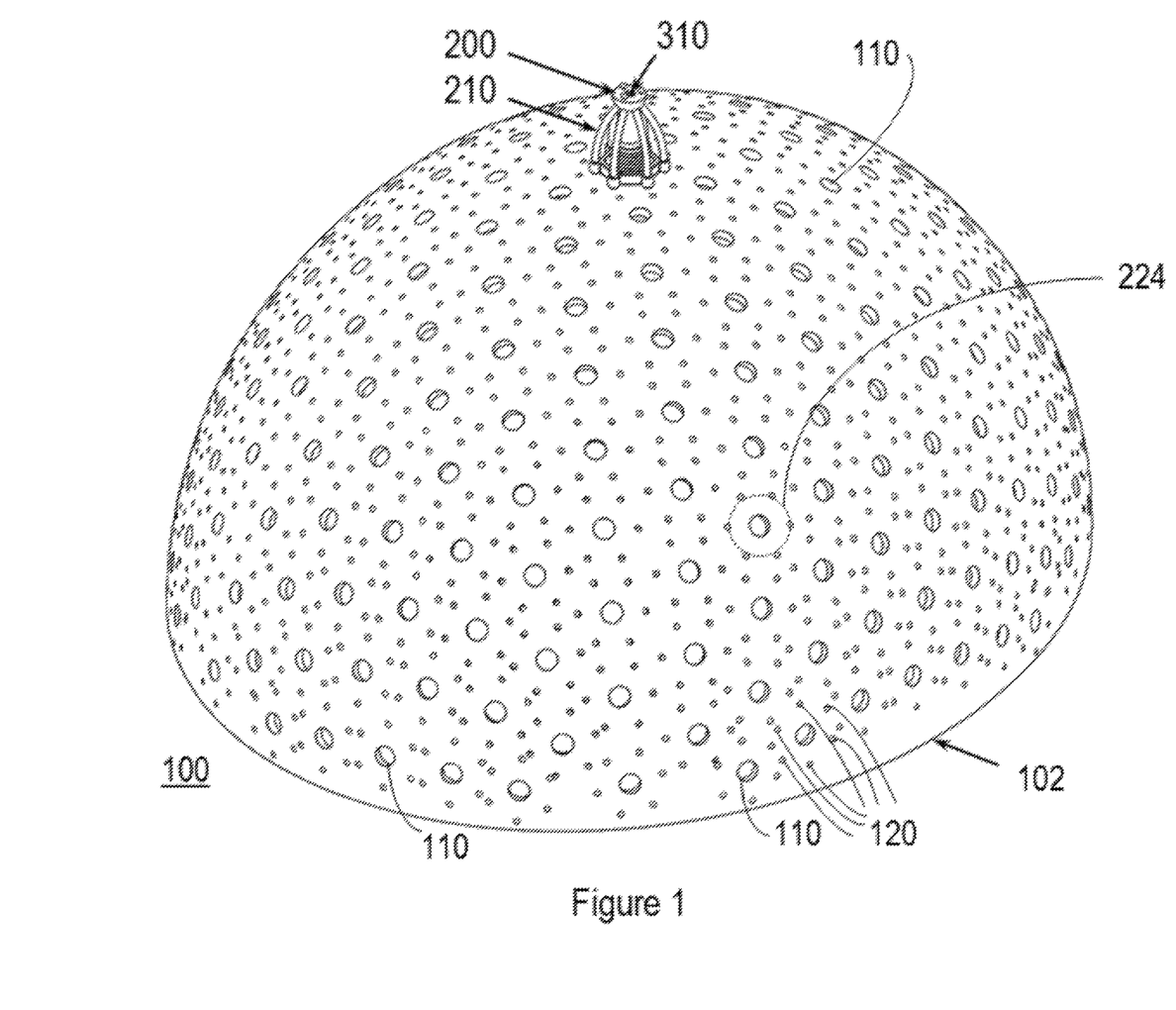
FIG. 1. Illustrates a perspective view of light therapy device for the scalp.

FIG. 1 presents a perspective view of an exemplary light therapy device for the scalp. The exemplary light therapy device discussed below is intended for illustrative purposes only. Variations of the light therapy device 100 are within the scope of this disclosure for other applications of light therapy to a body organ. A body organ can comprise an entirety of a body structure (such as a hand, leg, head, scalp, etc.). In addition, the body organ can comprise skin or tissue that is part of such a body structure.

A dome 102 is configured with a plurality of ferrule openings 110 and a plurality of holes 120 for a plurality of optical fiber or illumination assemblies 200, only one of which is shown for clarity, extending between an interior surface 104 to an exterior surface 106 of the dome 100. As noted herein, the illumination source can comprise an optical fiber having a source of illumination at the end of the fiber closest to the tissue. Alternatively, or in combination, the devices can include one or more projection elements, where each projection element comprises a distal portion having an illumination source configured to direct the electromagnetic energy to the body organ.

Figure 3:
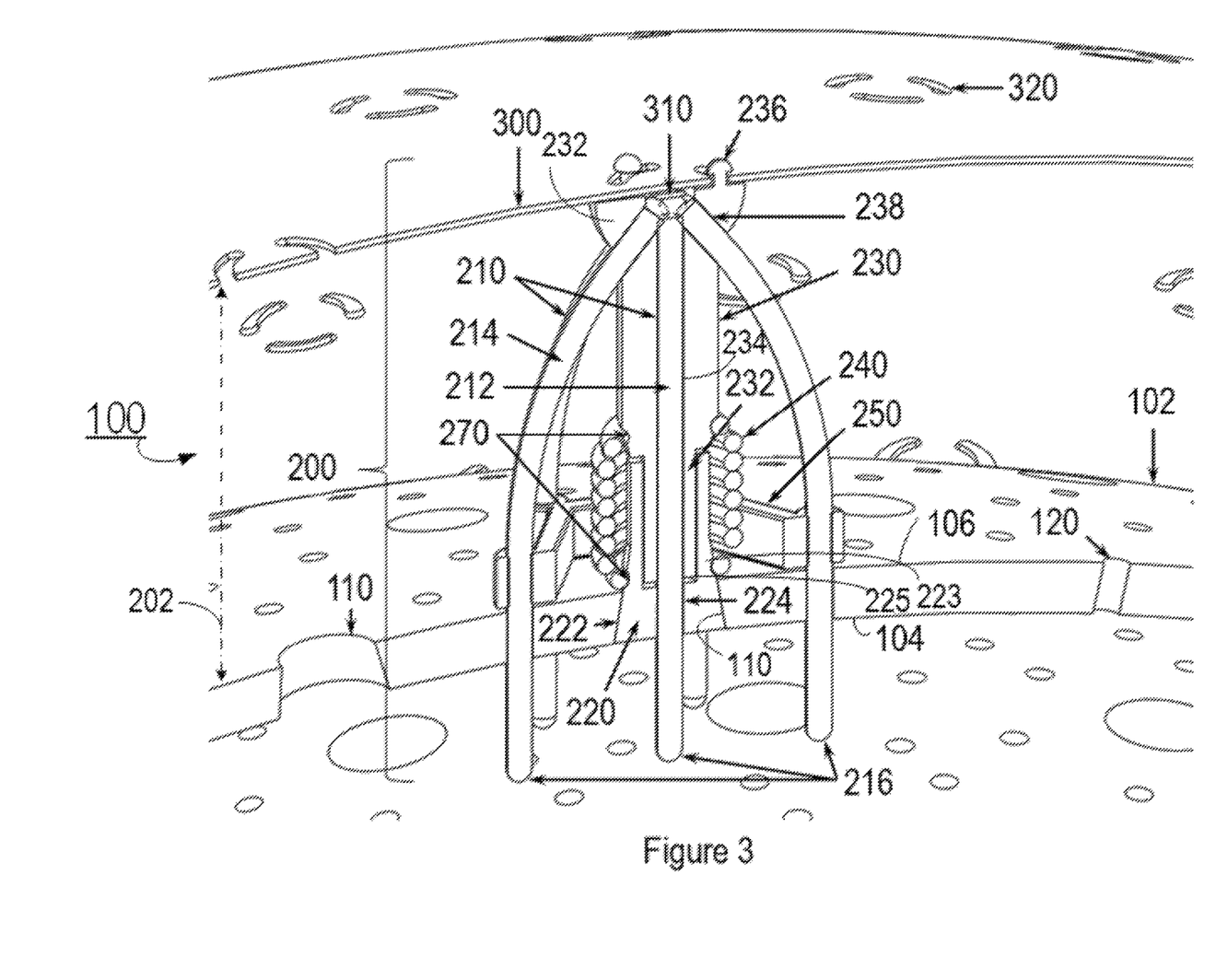
FIG. 3. Illustrates a close-up, cross-section, perspective view of flexible PCB, illumination assembly and dome alignment.

The ferrule openings 110 are configured with a taper from the interior surface 104 to the exterior surface 104 adapted to operably connect a tapered end 222 of a base 220 therein as shown in FIG. 3. The plurality of holes 120 are located adjacent to a ferrule opening 110 and configured in a dimension to be spaced apart such that the light from a plurality of optical illumination assemblies 2000 disposed in the ferrule opening 110 and holes 120 provide sufficient light therapy coverage over a treatment area and/or surface of the body organ in a substantially uniform manner. The optical fibers assemblies or illumination assemblies are independently biased so that the tips 216 of the optical fibers/projection elements 210 of each assembly can better conform to the shape of the head and/or be operably in contact with the body organ. This independent biasing allows for an improved device with multiple illumination sources that achieve a perpendicular approach to the target tissue. The independent biasing allows each assembly to conform to a contoured surface of the body organ without significantly affecting adjacent assemblies, which increases the ability of the adjacent assemblies to irradiate the tissue in a normal direction. Lambert's cosine law predicts that an illumination beam that is perpendicular to its target can achieve a higher rate of irradiance. In contrast, a beam that is offset from a perpendicular approach will have a greater degree of reflection off of the target area. Which means that a curved or contoured surface like the scalp (or any other contoured body organ) has a greater chance of being irradiated if the sources of illumination irradiate the scalp at a perpendicular angle. The independent biasing of the plurality of illumination assemblies can decrease the overall reflectance of light from a curved surface and increase the effectiveness or uniformity of the LLLT applied.

Figure 5:
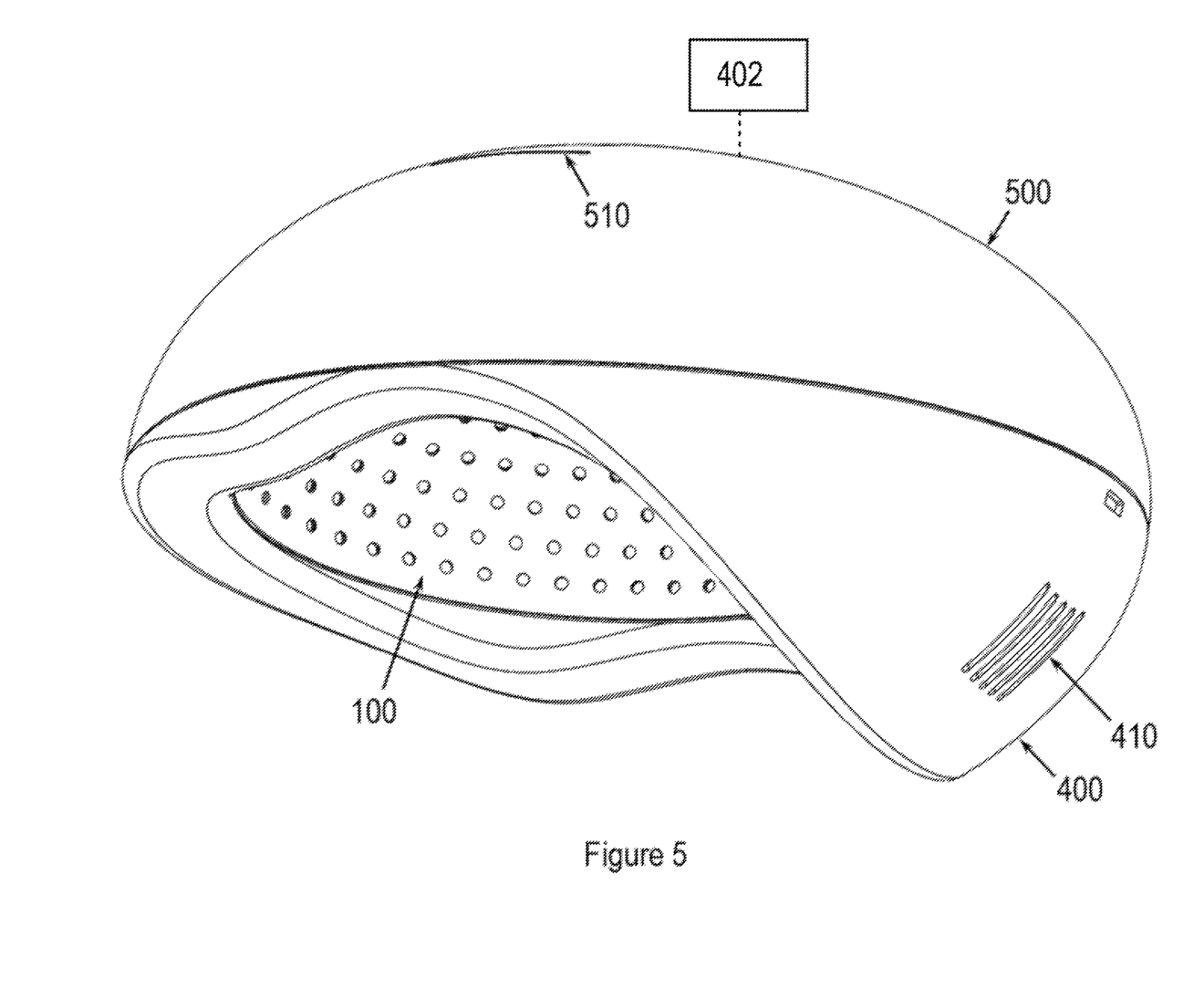
FIG. 5. Illustrates a close-up, cut-away, perspective view of flexible PCB, illumination assembly and dome alignment.
Figure 6:
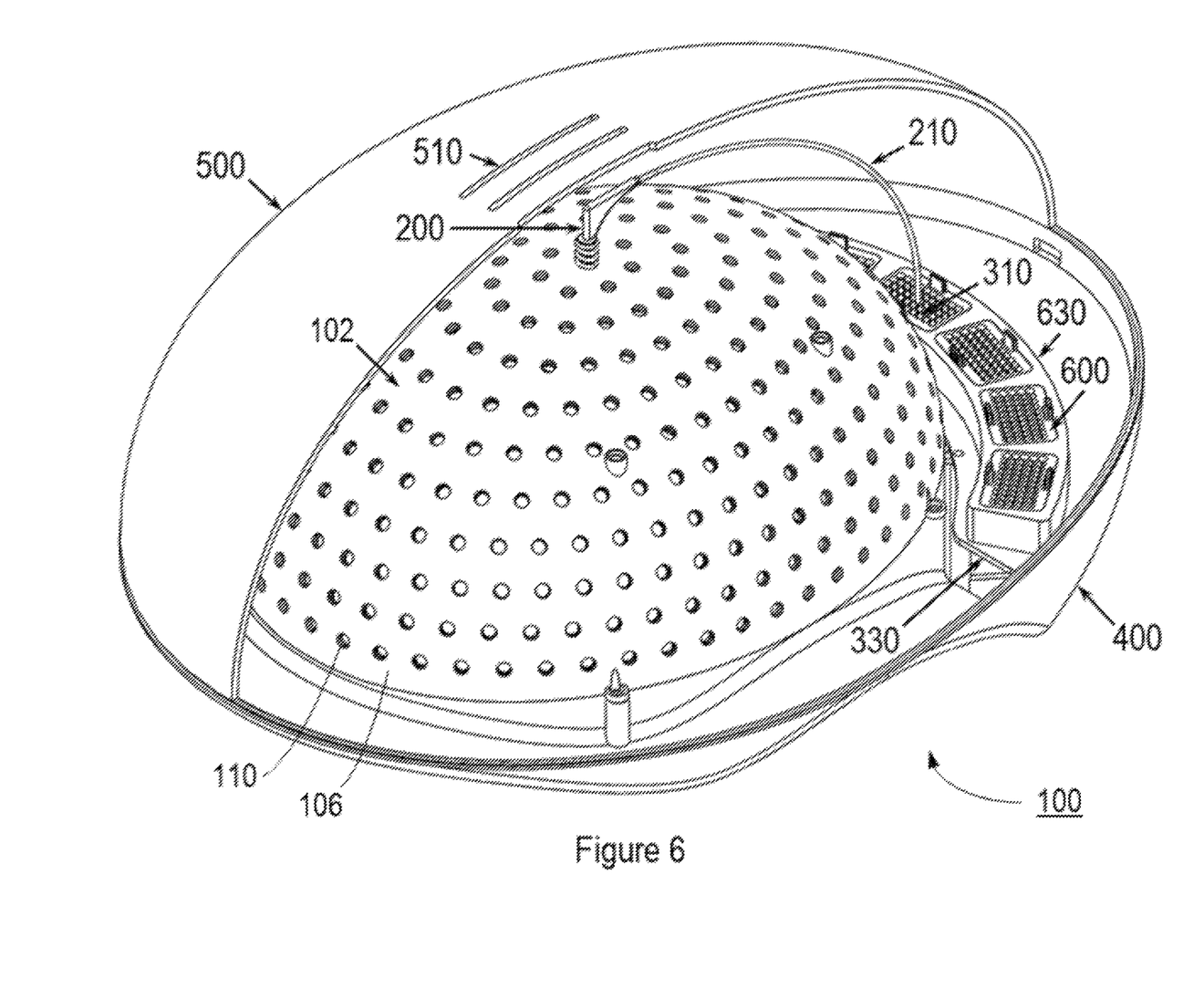
FIG. 6. Illustrates a perspective, cutaway view of alternative embodiment of light therapy device for the scalp.

The optical fibers/projection elements 210 are associated and optically coupled to a light source 310 situated above the dome 102. Advantageously, light therapy device 100 may dissipate any heat generated by a plurality of the light sources 310 to be located away from the body organ, i.e. the skin of a patient's scalp such as, for example, the heat is dissipated through vents 410, 510 as shown in FIGS. 5 and 6. Optionally, a cooling source 402 can be fluidly coupled to the device to cool any component within the device and/or tissue.

Figure 2:
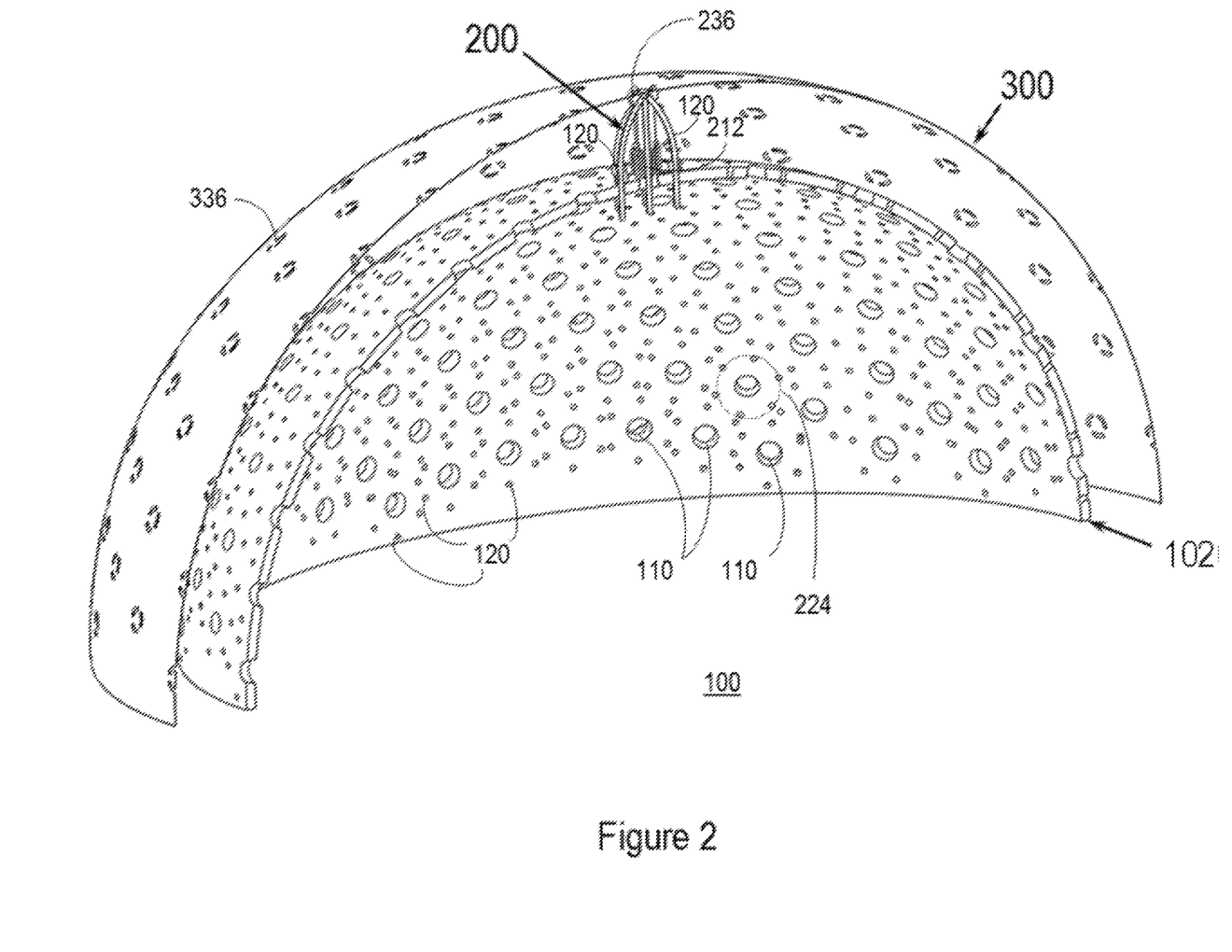
FIG. 2. Illustrates a cross-section, perspective view of light therapy device for the scalp with flexible PCB.

Referring to FIGS. 1-4, the light therapy device 100 may be formed having the light sources 310 disposed on a flexible printed circuit board (flex PCB) 300. The flex PCB 300 is configured to be located adjacent the dome 102 and wrapped at a predetermined offset distance and/or gap 202 around the dome 102, as shown in FIG. 2. The predetermined offset distance and/or gap 202 is configured by the dimension of the fiber/illumination assembly 200. The flex PCB 300 may be formed of suitable materials and/or construction that allows bending in a direction parallel to, and flexing in a direction normal to, the surface of the dome 102. The flex PCB 300 is configured with an electronic circuit to energize the light sources 310.

FIG. 3 illustrates the link from light source to skin achieved by the light therapy device 100. The optical fibers/projection elements 210 are coupled to the light source 310 by means of an optical fiber/illumination assembly 200. The optical fiber/illumination assembly 200 is attached at one end to the dome 102 and at the other end adjacent to the light sources 310 operably connected by the electrical circuit in the flex PCB 300. For example, one or more slots 320 may be formed in the flex PCB 300 configured to engage one or more locking posts 236 of the ferrule 230 as shown in FIGS. 1-3. In this manner, the optical fiber/illumination assembly 200 may be located adjacent to the light sources 310 thereby optically connecting so as to transmit light along the optical fibers/projection elements 210, 212 to the body organ.

According to an embodiment of the light therapy device 100, as is illustrated in FIGS. 1-3. For convenience, the variations are discussed as having an optical fiber. However, a projection element with an illumination source can be used in place of or in addition to the optical fiber assembly or fiber itself.

In FIGS. 1-3, the optical fiber assembly 200 comprises a base 220, a ferrule 230, a spring 240, a fiber collar 250, and one or more optical fibers 210. The base 220 may be configured with a base tube 224 along its longitudinal length, a tapered end 222 to be received in the dome 102, and a projecting proximal end 223 with a guide shaft 225 adapted to receive an inner tube 232 of the ferrule 230 therein. The ferrule 230 also may be configured with ferrule tube 234 along its longitudinal length for passing an axial optical fiber 212 there-through, whereby this centrally located, axial optical fiber 212 is allowed to move within the openings 224, 234 (e.g. to travel up and down) by means of aligning the pair of concentric base and ferrule tubes 224, 234 formed in the base 220 and ferrule 230. The other optical fibers 210 may be connected at one end in one or more fiber holes 238 formed in a base portion 232 of the ferrule 230 and, at points along the optical fibers 210, by a fiber collar 250, whereby these optical fibers 210 are fixed to the ferrule 230 in the base portion 232, are aligned with and pass through the plurality of fiber openings 220 in the dome 102 so as to slide freely there-through. Consequently, the free ends 216 of the optical fibers 210 and axial optical fiber 212 are configured to operatively connect to the body organ. Additionally, the base 220 and ferrule 230 are connected to each other by means of a biasing element 240 (e.g. a spring) that functions to provide a force to fiber optical assembly 200 so as to gently push the free ends 216 of each optical fibers 210, 212 into contact with the scalp. Accordingly, the light therapy device 100 advantageously provides light in direct contact with the body organ so as to guide light for light therapy directly from the light source 310 to the scalp or skin.

As shown in FIG. 3, the ferrule 230 is assembled to the base 224 by means of a spring 240 configured to be received in recesses 270 formed in the base and ferrule, whereby the spring 240 may snap-fit into the recesses 270 for ease of assembly. Once assembled, the spring 240 is configured to provide sufficient retention force on the recesses 270 such that the spring 240 remains attached and the biasing force allows the inner tube 232 of ferrule 230 to move in the guide shaft 225 of the base 220 during extension, for example, when connecting directly to the contour of the body organ that forces free ends 216 of the optical fibers 210, 212 away from the body organ. The base 224 comprises a tapered end 222, which is press fit into a tapered hole 110 extending between the interior and exterior surfaces 104, 106 formed in the dome 102. The spring 240 locks the proximal end 223 of the base 220 above the dome 102 thereby preventing the base 220 from disengaging or otherwise falling out of the tapered hole 110. The inner tube 232 is configured to slide into the guide shaft 225 of the base 220 thereby providing passive alignment of the axial optical fiber 212 relative to the tapered hole 110 in the dome 102. Similarly, the fiber collar 250 is configured to secure and/or align the optical fibers 210 in a precise array such that the optical fibers 210 may be inserted insert into, and move freely within, the fiber holes 120 formed in the dome 102.

As is illustrated in FIG. 3, the ferrule 230 is aligned to the light source 310 by means of slots 320 in the flex PCB 300. The slots 336 engage locking posts 236 disposed on a top end of a body portion 234 of the ferrule 230. The posts 236 are configured to engage the slots 336 positioned in a circular array such that, once engaged, the posts 236 may rotate within the slots 336 while keeping the ferrule 230 centered with respect to the light source 310. The fiber assembly 200 is adjustable as the posts 236 and slots 336 also are configured to provide for rotational alignment of the circular array of optical fibers 210 to the fiber holes 120 formed in the dome 102, as shown in FIG. 3.

Referring to FIGS. 1-3, the body portion 232 of the ferrule 230 comprises multiple fiber holes 238 which align the optical fibers 210 to the light source 310. In this embodiment, seven fibers are aligned to a light emitting diode (LED) 310: one axial optical fiber 212 along a lengthwise, longitudinal and/or vertical axis of the ferrule 230 and six optical fibers 210 arranged in a circular array 214 at an angle to the vertical axis sufficient to effectuate fiber-coupled light. At the proximal end each of the seven fibers, specifically, the optical fibers 210 and the axial optical fiber 212 are configured to capture a significant fraction of the optical power emitted by the light source 310. Furthermore, the positioning of the optical fibers 210 in the base portion 214 and the axial optical fiber 212 in the base tube 224 and ferrule tube 234 is such that the fiber-coupled light is substantially evenly distributed amongst the seven fibers. The axial optical fiber 212 is secured within a hole formed by the base tube 224 and the ferule tube 234 in the center of the ferrule 230, thereby remaining parallel to the axis of motion. Each optical fiber 210 in the circular fiber array 214 is bent by means of a fiber collar 250 such that the free distal end 216 is substantially parallel to the axial optical fiber 212. In this way, all seven fibers 210, 212 may travel freely in a direction parallel to the axis of the ferrule 230 that is arranged substantially normal to the surface of the dome 102.

As shown in FIG. 1, the light therapy device 100 consists of matching a circular array 214 of optical fibers 120 to any hole array 228 of the fiber holes 120 surrounding the tapered hole 110 in the dome 102. The circular fiber array 214 penetrates the matching hole array 228 such that all seven fibers 210, 212 travel simultaneously. As shown in FIGS. 2 and 3, the light therapy device 100 may be configured to limit fiber travel in a dimension in extent toward the distal end 216 by the mating of the concentric base 228 and ferrule tubes 234 formed in the base 220 and ferrule 230 (maximum fiber length below the dome 102), and at the proximal end 223 by the interior surface 104 of the dome 102 (fiber tips 216 flush with the dome 102). The tips 216 of the optical fibers 120 and axial optical fiber 212 may be shaped for patient comfort. The shape of the fiber tips 216 can also be configured to spread the light laterally to an area larger than the fiber diameter.

For example, as shown in FIG. 2, when a patient's head is placed within the dome 102 adjacent the inner surface 104 the scalp engages the extending fibers 120 and axial optical fiber 212 and pushes these radially outward, with each fiber array 214 flexing individually in a particular hole array 228 depending on the particular shape of the scalp. In this way, the fiber arrays 214 of the light therapy device 100 can conformally and simultaneously contact the entirety of the scalp. The optical fibers 120 and the axial optical fiber 212 are configured flexible to allow bending to accommodate a shift of position of the scalp with respect to the interior surface 104 of the dome 102, for example, bending slightly off-axis when moved on the scalp. Consequently, the light therapy device 100 may be integrated into a portable, wearable helmet as shown in FIG. 5.

Figure 4:
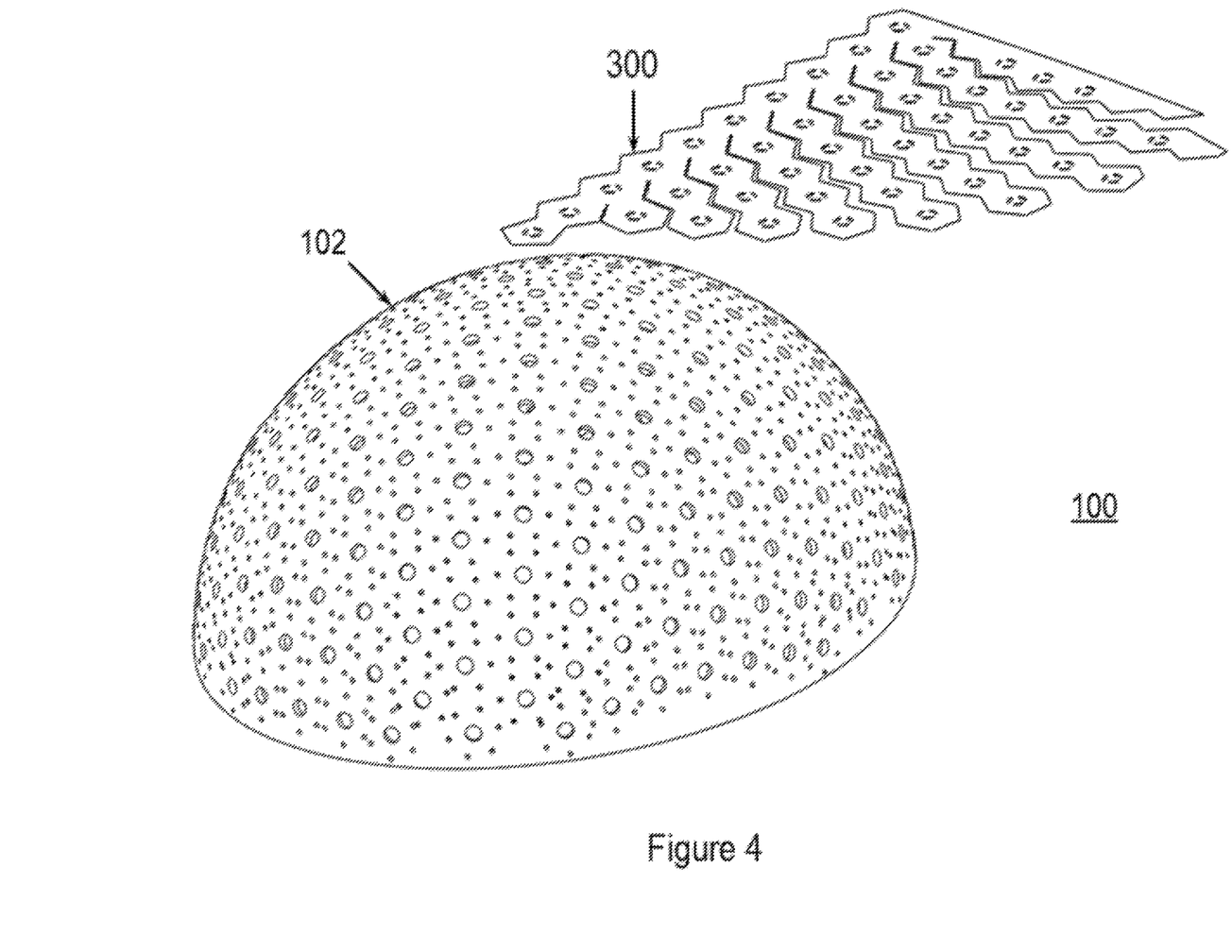
FIG. 4. Illustrates a perspective view of flattened flexible PCB and dome prior to assembly.

FIG. 4 displays one section of the flex PCB 300 in position above the dome 102 and prior to assembly. In an exemplary embodiment, the flex PCB 300 comprises a thin, flexible material that is cut in lines of relief to bend and/or to conform to the shape of the dome 102.

The dome 102 is affixed to a base 400, as illustrated in FIG. 5. The base contains a rigid PCB (not shown), which contains the control electronics. The flexible PCB containing the light sources is connected to the rigid PCB. The base can also contain one or more batteries (also not shown) which are capable of powering the device for the duration of the treatment. An outer shell 500, which may itself be either flexible or rigid, protects the flex PCB 300 and other elements of the light therapy device 100 from physical and other interference. The heat from the light sources and associated control electronics are dissipated by means of vents in the base 410 and outer shell 510, which draw cool air in from the bottom and allow heated air to escape from the top.

Figure 7:
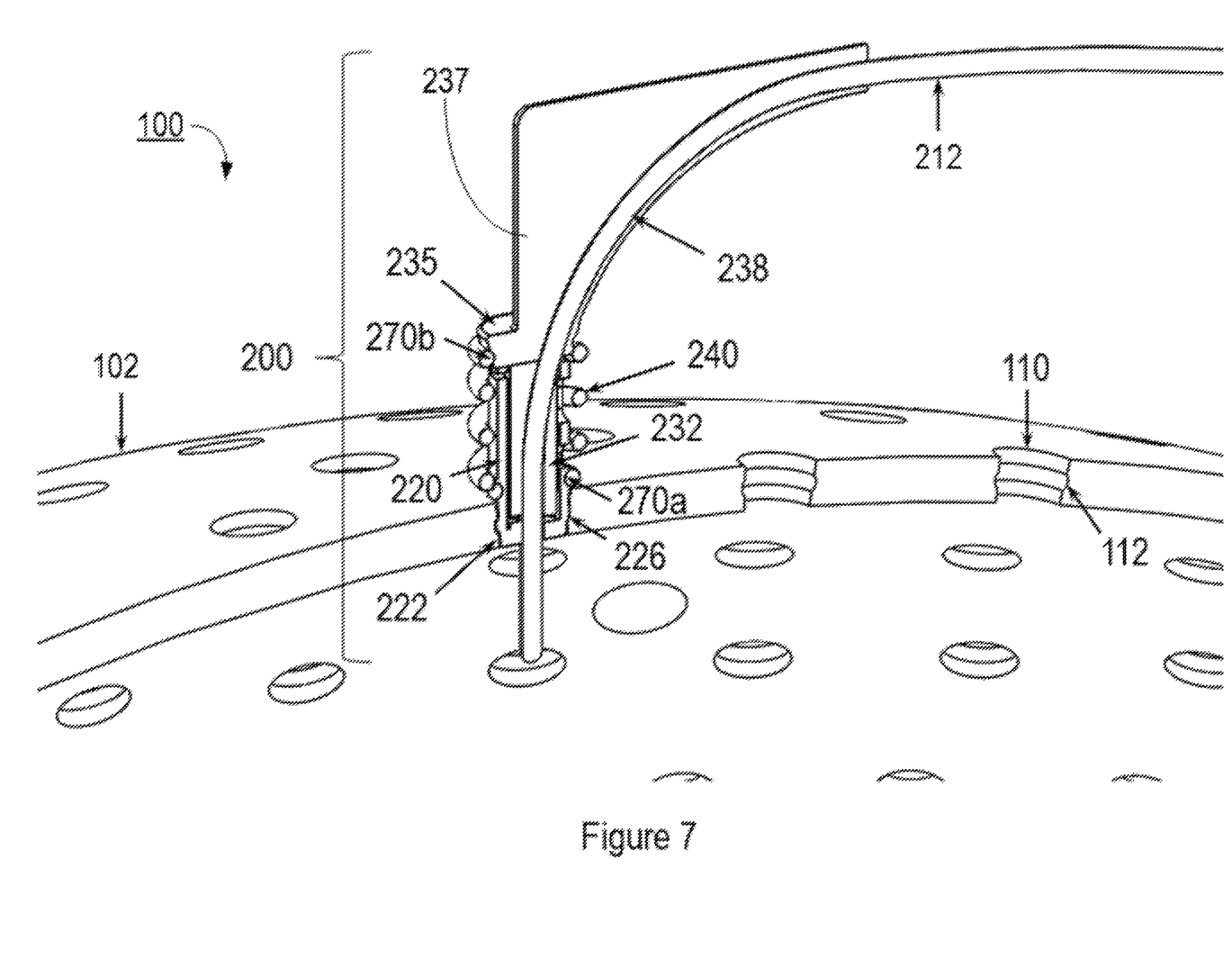
FIG. 7. Illustrates a close-up, cross-section, perspective view of the illumination assembly and dome alignment.
Figure 8:
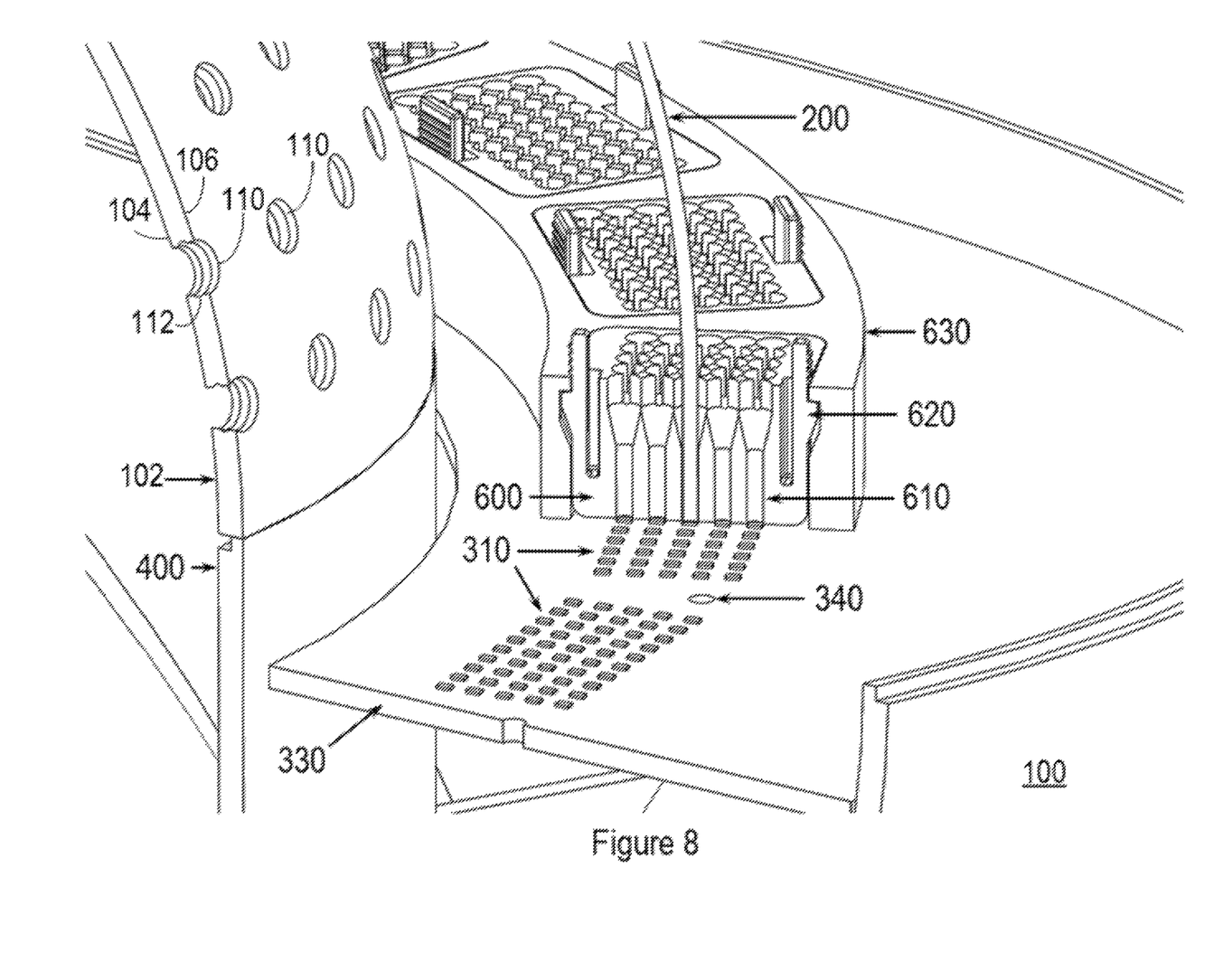
FIG. 8. Illustrates a close-up, cut-away, perspective view of rigid PCB, ferrule, and alignment structure.

Referring to FIGS. 6 through 8, another embodiment of a light therapy device 100 provides direct contact between the body organ and the optical fiber 120 using an alternative design. The light therapy device 100 comprises a ferrule 235, an array of light sources 310 and associated control electronics (not shown) mounted on a rigid PCB 330 that may be secured to the base 400 at the back of the dome 102. The dome 102 similarly contains tapered holes 110 formed by the opening extending between an interior surface 104 and an exterior surface 106. The tapered holes 110 are configured to receive a plurality of optical fiber assemblies 200, only one of which is shown in FIG. 6. Axial optical fibers 212 disposed in the ferrule 235 are configured so that the tips 216 of the axial optical fibers 212 conform to the shape of the head and/or body organ. The axial optical fibers 212 are coupled to the light sources 310 at the back of the dome 102 by means of an adapter 630. The adapter 630 may be configured to fasten and secure to a rigid printed circuit board (PCB) 330 by interlocking tabs of a leaf spring latch 620 in a notch formed in the adapter 630 as shown in FIG. 8. The rigid PCB 330 is configured with the electrical circuit for the light sources 310 and control electronics. A source of electrical power may be configured into the rigid PCB 300 assembly such as, for example, batteries (not shown). The source of electrical power is configured capable of powering the light therapy device 100 for the duration of the treatment.

As shown in FIGS. 6 and 7, the dome 102 is affixed to a base 400 and an outer shell 500. The heat from the light sources 310 and associated driver electronics are mitigated by means of one or more vents 410 and 510 in the helmet. These one or more vents 410 in the helmet base, as shown in FIG. 5 are configured to draw cool air in, while vents 510 in the helmet top allow heated air to escape. The helmet may be formed with an outer shell configured in the helmet base and helmet top portions. The outer shell may be formed flexible and/or rigid, as well as formed to protect the flex PCB 300 and other elements of the light therapy device 100 from physical and other interference.

As is illustrated in FIG. 7, the light therapy device 100 comprises an optical fiber assembly 200 attached using tapered holes 212 in the dome 102. The fiber assembly comprises a base 220, a ferrule 235, a flange guide 237, a spring 240 and one or more optical axial optical fibers 212. The ferrule 235 comprises a bent tube 238 formed in the flange guide 237 that directs the axial optical fiber 212 toward the rear of the dome 102 for connecting to the rigid PCB 300 using the adapter 600. The movement or action of the axial optical fiber 212 can be achieved by means of inner 232 and outer 220 tubes formed by the base 222 and ferrule 235 which slide concentrically with respect to each other. The inner 232 and outer 220 tubes are biased by means of a biasing element 240, e.g. a spring. The light therapy device 100 may be configured with a biasing force selected so that an aggregate spring force of all optical fiber assemblies 200 allow all axial optical fibers 212 to make contact with the scalp simultaneously.

As shown in FIGS. 6-8, the ferrule 235 is attached to the dome 102 by means of a tapered base 222 and is configured to operably connect to the tapered holes 110. The tapered base 222 comprises slight protrusions 226 configured to slidably, snap fit to a recesses 112 in the tapered holes 110, thereby allowing rotation, and preventing the tapered base 222 from dislodging and/or otherwise falling out. The ferrule 230 is secured to the tapered base 222 by means of a spring 240 configured to slidably, snap fit into a recess 270*a* configured in the tapered base 222 and a recess 270*b* formed in the ferrule 235. Once assembled, the biasing element 240 (e.g. spring) is configured to have sufficient retention force on the recesses 270*a*, 270*b* such that it remains attached at each end during extension.

As shown in FIG. 8, the light therapy device 100 comprises one or more arrays of light sources 310 and their control electronics (not shown) mounted on a rigid PCB 330, which is secured to the base 400 at the back of the dome 102. A multi-fiber ferrule (MFF) 600 can be configured to align the light sources 310 to each axial optical fiber 212 disposed in one or more fiber openings or an array of fiber holes 610 by means of an adapter 630 secured to the rigid PCB 330. The adapter 630 may be configured to align the one or more fiber openings 610 over arrays light sources 310 (e.g. rows of individual light sources 310) and fiber openings 610. The adapter 630 may connect to align the ends of each of the axial optical fibers 212 disposed in fiber openings 610 adjacent to the light source arrays 310 by means of precision screw holes 340 in the PCB. The MFF 600 comprises the array of fiber holes 610 populated by receiving a plurality of axial optical fibers 212 herein. The MFF 600 is secured to the adapter 630 by leaf spring latches 620. Advantageously, the latches 620 may act as leaf springs to center the MFF 600 within the adapter 630, thereby providing fine alignment of the fiber openings 610 adjacent to the light sources 310.

The devices and methods described herein can optimize cell proliferation (i.e. growth of hair) with low doses over longer periods of time. It is believed that LLLT/PBM creates a dose dependent effect so each dose builds on the previous treatment (and the Arndt-Schulz Law means that too much dose has suppressive effects). Therefore, the assemblies disclosed herein allow for a uniform treatment applied in a manner that avoids the suppressive effects of over-treatment. In one example, it was found that 14-20 minutes applied every few days was sufficient to penetrate to the depth of the hair follicle within the skin.

The previous description of the disclosed embodiments is provided to enable any person skilled in the art to make or use the present invention. Various modifications to these embodiments will be readily apparent to those skilled in the art, and the generic principles defined herein can be applied to other embodiments without departing from the spirit or scope of the invention. For example, a wide variety of materials may be chosen for the various components of the embodiments. It is therefore desired that the present embodiments be considered in all respects as illustrative and not restrictive, reference being made to the appended claims as well as the foregoing descriptions to indicate the scope of the invention.

We claim:

1. A device for positioning over and applying electromagnetic energy to a body organ, the device comprising:
   - a support structure forming a contoured shape, where an interior space of the contoured shape is adapted for placement over the body organ;
   - a dome structure located within the interior space of the contoured shape and spaced from the support structure, the dome structure comprising a plurality of openings;
   - a plurality of projection assemblies each having a projection element surrounded by a plurality of auxiliary projection elements, where each projection element and each of the plurality of auxiliary projection elements comprises a distal portion having an illumination source configured to direct the electromagnetic energy to the body organ, where the distal portion is flexible to accommodate bending upon a shift in the support structure; and
   - each of the plurality of projection assemblies can extend through the plurality of openings in the dome structure, and where each of the plurality of projection assemblies is configured to be independently biased at a back side of the dome structure such that each of the plurality of projection assemblies can extend by a length that is independent of the remaining plurality of projection assemblies.

2. The device of claim 1, where the distal portion of each projection element and each of the plurality of auxiliary projection elements is flexible to accommodate bending upon a shift in the support structure.

3. The device of claim 2, where the projection element is centrally located relative to each of the plurality of auxiliary projection elements.

4. The device of claim 1, where the illumination source comprises a source of electromagnetic energy on the distal portion of the projection element.

5. The device of claim 1, where a source of electromagnetic energy is located remotely from the illumination source and the projection element is configured to transmit electromagnetic energy therein to the illumination source.

6. The device of claim 1, wherein the biasing element is located on a surface of the support structure opposite to the interior space of the contoured shape.

7. The device of claim 1, where the illumination source is located on a distal end of the projection element.

8. The device of claim 7, where the distal end of the projection element is atraumatic such that it does not penetrate the surface of the body organ.

9. The device of claim 1, where the projection element is located within a base member and where the base member is coupled to the biasing element.

10. The device of claim 1, where the projection element comprises an optical fiber.

11. The device of claim 1, wherein the support structure is located within an outer shell.

12. The device of claim 11, where the outer shell is vented.

13. The device of claim 1, further comprising a coil spring coupled to the projection assembly.

14. The device of claim 1, where the illumination source comprises a light emitting diode.

15. The device of claim 1, further comprising at least one cooling mechanism coupled to the support structure.

16. The device of claim 1, where the distal portion of the projection element is atraumatic to prevent penetration into tissue.

17. A method of applying electromagnetic energy to a body organ, the method comprising:
   - positioning a support structure having a contoured shape over the body organ, where an interior space of the contoured shape comprises a plurality of projection assemblies each having a plurality of projection elements, each projection element having an illumination source;
   - each of the projection assemblies being independently biased through the guide openings such that each of the plurality of projection elements for each projection assembly moves together while each additional projection assembly is biased independently; and
   - applying electromagnetic energy through each of the illumination sources of the projection element adjacent to the contoured surface of the body organ.

18. The method of claim 16, further comprising directing a source of cooling towards the contoured surface of the body organ.

19. The method of claim 16, where positioning the support structure over the body organ comprises positioning the support structure over a scalp of a patient.

20. The method of claim 16, wherein applying electromagnetic energy comprises applying electromagnetic energy selected from the group consisting of a coherent light, an incoherent light source, and a combination thereof.

21. A device for positioning over and applying electromagnetic energy to a body organ, the device comprising:
   a support structure forming a contoured shape, where an interior space of the contoured shape is adapted for placement over the body organ;
   a plurality of projection assemblies each having a group of projection elements, where each of the plurality of projection elements comprises a distal portion having an illumination source configured to direct the electromagnetic energy to the body organ; and
   each of the plurality of projection assemblies is independently biased towards the interior space of the contoured shape allowing the group of projection elements associated with each of the plurality of projection assemblies to move together proximally upon engaging a surface of the body organ wherein each of the plurality of projection assemblies is configured to be biased independently from the plurality of projection assemblies.

* * * * *